US010641773B2

(12) United States Patent
Mochizuki et al.

(10) Patent No.: US 10,641,773 B2
(45) Date of Patent: May 5, 2020

(54) BIOMARKER FOR DIAGNOSIS OF EXTRAHEPATIC BILE DUCT CARCINOMA, INTRAHEPATIC BILE DUCT CARCINOMA, OR GALLBLADDER CARCINOMA

(71) Applicant: SHIZUOKA PREFECTURE, Shizuoka, Shizuoka (JP)

(72) Inventors: Tohru Mochizuki, Sunto-gun (JP); Keiichi Ohshima, Sunto-gun (JP); Keiichi Hatakeyama, Sunto-gun (JP); Ken Yamaguchi, Sunto-gun (JP); Kanako Nakao, Shinjuku-ku (JP)

(73) Assignee: SHIZUOKA PREFECTURE, Shizuoka (JP)

( * ) Notice: Subject to any disclaimer, the term of this patent is extended or adjusted under 35 U.S.C. 154(b) by 0 days.

(21) Appl. No.: 15/656,896

(22) Filed: Jul. 21, 2017

(65) Prior Publication Data

US 2018/0080935 A1     Mar. 22, 2018

Related U.S. Application Data

(63) Continuation of application No. PCT/JP2016/003451, filed on Jul. 25, 2016.

(51) Int. Cl.
*G01N 33/574*     (2006.01)

(52) U.S. Cl.
CPC ............... *G01N 33/57438* (2013.01); *G01N 2333/70596* (2013.01); *G01N 2800/7028* (2013.01)

(58) Field of Classification Search
None
See application file for complete search history.

(56) References Cited

U.S. PATENT DOCUMENTS

2007/0071758 A1   3/2007  Markel
2012/0122122 A1*  5/2012  Markel ............... G01N 33/5044
                                                      435/7.24

FOREIGN PATENT DOCUMENTS

| JP | 2012-525142 | 10/2012 |
| JP | 2015-53906 | 3/2015 |
| JP | 2015-139440 | 8/2015 |
| WO | WO 2015/075710 | 5/2015 |
| WO | WO 2015/182580 | 12/2015 |

OTHER PUBLICATIONS

Markel et al (Oncotarget, Feb. 2016, 7:17886-17895).*
Yu et al (PLoS One, Apr. 2016, 11(4):e0153601; p. 1-12).*
O'Brien et al (Clinical Cancer Research, 2015, 21:622-631).*
Ganeshan et al (World Journal of Radiology, 2012, 4:345-352).*
Kondo et al (Journal of Gastroenterology, 2001, 36:470-475).*
Zhou et al (BMC Cancer, 2013, 13:359).*
Anderson et al (The Oncologist, 2004, 9:43-57).*
Simeone et al (Pancreas, 2007, 34:436-443).*
Sivan et al (Clinical and Developmental Immunology, 2012, Article ID 290536; 8 pages).*
Wang et al (World J Gastroenterology, 2014, 20:4085-4092).*
Lee et al (J Korean Medical Science, 2014, 29:1333-1340).*
Cruz et al., "Loss of Carcinoembryonic Antigen-Related Cell Adhesion Molecule 1 Expression is an Adverse Prognostic Factor in Hepatocellular Carcinoma," *American Cancer Society*, 2005; 104(2): 354-360.
Hinoda et al., "Transcription of Biliary Glycoprotein I Gene in Malignant and Non-Malignant Human Liver Tissues," *Int. J. Cancer*, 1990; 45: 875-878.
Notice by the Director of Shizuoka Cancer Center Hospital, 2015 (English translation provided).
Prall et al., "CD66a (BGP), an Adhesion Molecule of the Carcinoembryonic Antigen Family, Is Expressed in Epithelium, Endothelium, and Myeloid Cells in a Wide Range of Normal Human Tissues," *Journal of Histochemistry and Cytochemistry*, 1996; 44(1): 35-41.
Publishing Committee of the Clinical Practice Guidelines for the Management of Biliary Tract Cancers of the Japanese Society of Hepato-Biliary-Pancreatic Surgery, "Evidence-Based Clinical Guidelines for the Management of Biliary Tract Cancers," *Igaku Tosho Shuppan*, 2nd ed., Nov. 1, 2014, 38-39 (English translation provided).
Simeone et al., "CEACAM1, a Novel Serum Biomarker for Pancreatic Cancer," *Pancreas*, 2007; 34: 436-443.
Uchino et al., "Carcinoembryonic Antigen (CEA) and CEA-Related Substances in the Bile of Patients with Biliary Diseases," *American Journal of Surgery*, 1994; 167: 306-308.
Briggs et al., "Prognostic molecular markers in cholangiocarcinoma: A Systematic Review," *European Journal of Cancer*, 45:33-47, (2009).
European Search Report issued in European Application No. 17182572, dated Nov. 27, 2017.
Kondo et al., "Measurement of circulating biliary glycoprotein (CD66a) in liver disease," *J. Gastroenterol*. 36:470-475, (2001).

* cited by examiner

*Primary Examiner* — Laura B Goddard
(74) *Attorney, Agent, or Firm* — Norton Rose Fulbright US LLP

(57)     ABSTRACT

An object of the present invention is to provide a method for collecting highly accurate data for diagnosis, useful in diagnosing the presence or absence of extrahepatic bile duct carcinoma, intrahepatic bile duct carcinoma, or gallbladder carcinoma, and a kit for diagnosis.
When the concentration of CEACAM1 in a blood sample collected from a test subject is detected using a kit for diagnosis comprising an antibody specifically binding to CEACAM1 or a labeled product thereof, or the like and the CEACAM1 concentration is higher than the concentration of CEACAM1 in a blood sample derived from a non-carcinoma control subject or higher than a certain threshold value (cutoff value), data can be collected for diagnosing the test subject as having a high possibility of having extrahepatic bile duct carcinoma, intrahepatic bile duct carcinoma, or gallbladder carcinoma.

6 Claims, 6 Drawing Sheets

Specification includes a Sequence Listing.

SEQUENCE LISTING

```
<160> NUMBER OF SEQ ID NOS: 6

<210> SEQ ID NO 1
<211> LENGTH: 464
<212> TYPE: PRT
<213> ORGANISM: Homo sapiens
<220> FEATURE:
<221> NAME/KEY: MISC_FEATURE
<223> OTHER INFORMATION: CEACAM1 isoform 2 precursor

<400> SEQUENCE: 1

Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Leu Val His Asn Leu Pro Gln Gln Leu Phe Gly
    50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175
```

```
Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
            245                 250                 255

Leu Ser Cys Tyr Ala Ala Ser Asn Pro Pro Ala Gln Tyr Ser Trp Leu
        260                 265                 270

Ile Asn Gly Thr Phe Gln Gln Ser Thr Gln Glu Leu Phe Ile Pro Asn
    275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
            325                 330                 335

Val Thr Gly Asp Lys Asp Ser Val Asn Leu Thr Cys Ser Thr Asn Asp
        340                 345                 350

Thr Gly Ile Ser Ile Arg Trp Phe Phe Lys Asn Gln Ser Leu Pro Ser
    355                 360                 365

Ser Glu Arg Met Lys Leu Ser Gln Gly Asn Thr Thr Leu Ser Ile Asn
370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
            405                 410                 415

Asn Ala Leu Pro Gln Glu Asn Gly Leu Ser Pro Gly Ala Ile Ala Gly
        420                 425                 430

Ile Val Ile Gly Val Val Ala Leu Val Ala Leu Ile Ala Val Ala Leu
    435                 440                 445

Ala Cys Phe Leu His Phe Gly Lys Thr Gly Ser Ser Gly Pro Leu Gln
    450                 455                 460

<210> SEQ ID NO 2
<211> LENGTH: 430
<212> TYPE: PRT
<213> ORGANISM: Homo sapiens
<220> FEATURE:
<221> NAME/KEY: MISC_FEATURE
<223> OTHER INFORMATION: CEACAM1 isoform 4 precursor

<400> SEQUENCE: 2

Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Leu Val His Asn Leu Pro Gln Gln Leu Phe Gly
    50                  55                  60
```

Tyr Ser Trp Tyr Lys Gly Glu Arg Val Asp Gly Asn Arg Gln Ile Val
 65                  70                  75                  80

Gly Tyr Ala Ile Gly Thr Gln Gln Ala Thr Pro Gly Pro Ala Asn Ser
             85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
            115                 120                 125

Leu Val Asn Glu Glu Ala Thr Gly Gln Phe His Val Tyr Pro Glu Leu
            130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
                180                 185                 190

Leu Ser Asn Gly Asn Arg Thr Leu Thr Leu Leu Ser Val Thr Arg Asn
            195                 200                 205

Asp Thr Gly Pro Tyr Glu Cys Glu Ile Gln Asn Pro Val Ser Ala Asn
            210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
                260                 265                 270

Ile Asn Gly Thr Phe Gln Gln Ser Thr Gln Glu Leu Phe Ile Pro Asn
            275                 280                 285

Ile Thr Val Asn Asn Ser Gly Ser Tyr Thr Cys His Ala Asn Asn Ser
            290                 295                 300

Val Thr Gly Cys Asn Arg Thr Thr Val Lys Thr Ile Ile Val Thr Asp
305                 310                 315                 320

Asn Ala Leu Pro Gln Glu Asn Gly Leu Ser Pro Gly Ala Ile Ala Gly
                325                 330                 335

Ile Val Ile Gly Val Val Ala Leu Val Ala Leu Ile Ala Val Ala Leu
            340                 345                 350

Ala Cys Phe Leu His Phe Gly Lys Thr Gly Arg Ala Ser Asp Gln Arg
            355                 360                 365

Asp Leu Thr Glu His Lys Pro Ser Val Ser Asn His Thr Gln Asp His
            370                 375                 380

Ser Asn Asp Pro Pro Asn Lys Met Asn Glu Val Thr Tyr Ser Thr Leu
385                 390                 395                 400

Asn Phe Glu Ala Gln Gln Pro Thr Gln Pro Thr Ser Ala Ser Pro Ser
                405                 410                 415

Leu Thr Ala Thr Glu Ile Ile Tyr Ser Glu Val Lys Lys Gln
            420                 425                 430

<210> SEQ ID NO 3
<211> LENGTH: 461
<212> TYPE: PRT
<213> ORGANISM: Homo sapiens
<220> FEATURE:
<221> NAME/KEY: MISC_FEATURE
<223> OTHER INFORMATION: CEACAM1 isoform 3 precursor

<400> SEQUENCE: 3

```
Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Val His Asn Leu Pro Gln Gln Leu Phe Gly
    50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Arg Gln Asn Leu Thr Met Leu Pro Arg Leu Asp Ser Asn Ser Trp Ala
                325                 330                 335

Gln Ala Ile Leu Pro Ser Val Ser Gln Ser Ala Glu Ile Thr Asp Asn
            340                 345                 350

Ala Leu Pro Gln Glu Asn Gly Leu Ser Pro Gly Ala Ile Ala Gly Ile
        355                 360                 365

Val Ile Gly Val Val Ala Leu Val Ala Leu Ile Ala Val Ala Leu Ala
    370                 375                 380

Cys Phe Leu His Phe Gly Lys Thr Gly Arg Ala Ser Asp Gln Arg Asp
385                 390                 395                 400

Leu Thr Glu His Lys Pro Ser Val Ser Asn His Thr Gln Asp His Ser
                405                 410                 415
```

```
Asn Asp Pro Pro Asn Lys Met Asn Glu Val Thr Tyr Ser Thr Leu Asn
            420                 425                 430

Phe Glu Ala Gln Gln Pro Thr Gln Pro Thr Ser Ala Ser Pro Ser Leu
        435                 440                 445

Thr Ala Thr Glu Ile Ile Tyr Ser Glu Val Lys Lys Gln
    450                 455                 460

<210> SEQ ID NO 4
<211> LENGTH: 368
<212> TYPE: PRT
<213> ORGANISM: Homo sapiens
<220> FEATURE:
<221> NAME/KEY: MISC_FEATURE
<223> OTHER INFORMATION: CEACAM1 isoform 5 precursor

<400> SEQUENCE: 4

Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Leu Val His Asn Leu Pro Gln Gln Leu Phe Gly
    50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Asp
305                 310                 315                 320
```

```
Asn Ala Leu Pro Gln Glu Asn Gly Leu Ser Pro Gly Ala Ile Ala Gly
            325                 330                 335

Ile Val Ile Gly Val Val Ala Leu Val Ala Leu Ile Ala Val Ala Leu
            340                 345                 350

Ala Cys Phe Leu His Phe Gly Lys Thr Gly Ser Ser Gly Pro Leu Gln
            355                 360                 365

<210> SEQ ID NO 5
<211> LENGTH: 468
<212> TYPE: PRT
<213> ORGANISM: Homo sapiens
<220> FEATURE:
<221> NAME/KEY: MISC_FEATURE
<223> OTHER INFORMATION: CEACAM1 isoform 6 precursor

<400> SEQUENCE: 5

Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
            35                  40                  45

Lys Glu Val Leu Leu Leu Val His Asn Leu Pro Gln Gln Leu Phe Gly
        50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
            115                 120                 125

Leu Val Asn Glu Glu Ala Thr Gly Gln Phe His Val Tyr Pro Glu Leu
        130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320
```

-continued

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
            340                 345                 350

Thr Gly Ile Ser Ile Arg Trp Phe Phe Lys Asn Gln Ser Leu Pro Ser
        355                 360                 365

Ser Glu Arg Met Lys Leu Ser Gln Gly Asn Thr Thr Leu Ser Ile Asn
    370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
                405                 410                 415

Asn Ala Leu Pro Gln Glu Asn Gly Leu Ser Pro Gly Ala Ile Ala Gly
            420                 425                 430

Ile Val Ile Gly Val Val Ala Leu Val Ala Leu Ile Ala Val Ala Leu
        435                 440                 445

Ala Cys Phe Leu His Phe Gly Lys Thr Gly Arg Thr Thr Pro Met Thr
    450                 455                 460

His Leu Thr Arg
465

<210> SEQ ID NO 6
<211> LENGTH: 526
<212> TYPE: PRT
<213> ORGANISM: Homo sapiens
<220> FEATURE:
<221> NAME/KEY: MISC_FEATURE
<223> OTHER INFORMATION: CEACAM1 isoform 1 precursor

<400> SEQUENCE: 6

Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Leu Val His Asn Leu Pro Gln Gln Leu Phe Gly
    50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

```
Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
                260                 265                 270

Ile Asn Gly Thr Phe Gln Gln Ser Thr Gln Glu Leu Phe Ile Pro Asn
                275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
                340                 345                 350

Thr Gly Ile Ser Ile Arg Trp Phe Phe Lys Asn Gln Ser Leu Pro Ser
                355                 360                 365

Ser Glu Arg Met Lys Leu Ser Gln Gly Asn Thr Thr Leu Ser Ile Asn
    370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
                405                 410                 415

Asn Ala Leu Pro Gln Glu Asn Gly Leu Ser Pro Gly Ala Ile Ala Gly
                420                 425                 430

Ile Val Ile Gly Val Val Ala Leu Val Ala Leu Ile Ala Val Ala Leu
                435                 440                 445

Ala Cys Phe Leu His Phe Gly Lys Thr Gly Arg Ala Ser Asp Gln Arg
    450                 455                 460

Asp Leu Thr Glu His Lys Pro Ser Val Ser Asn His Thr Gln Asp His
465                 470                 475                 480

Ser Asn Asp Pro Pro Asn Lys Met Asn Glu Val Thr Tyr Ser Thr Leu
                485                 490                 495

Asn Phe Glu Ala Gln Gln Pro Thr Gln Pro Thr Ser Ala Ser Pro Ser
                500                 505                 510

Leu Thr Ala Thr Glu Ile Ile Tyr Ser Glu Val Lys Lys Gln
                515                 520                 525
```

BIOMARKER FOR DIAGNOSIS OF EXTRAHEPATIC BILE DUCT CARCINOMA, INTRAHEPATIC BILE DUCT CARCINOMA, OR GALLBLADDER CARCINOMA

TECHNICAL FIELD

The present invention relates to a method for collecting data for diagnosing extrahepatic bile duct carcinoma, intrahepatic bile duct carcinoma, or gallbladder carcinoma (hereinafter, these carcinomas are sometimes collectively referred to as "extrahepatic bile duct carcinoma or the like"), and a kit for diagnosing extrahepatic bile duct carcinoma or the like for use in the method.

BACKGROUND ART

The bile duct is a duct guiding bile produced in the liver into the duodenum and is roughly classified into the intrahepatic bile duct in the liver and the extrahepatic bile duct outside the liver. The extrahepatic bile duct is linked to the gallbladder for temporarily storing and concentrating bile via the gallbladder duct. The extrahepatic bile duct at which the extrahepatic bile duct and the gallbladder duct merge is called the common bile duct, and the intrahepatic bile duct, the extrahepatic bile duct, and the gallbladder are collectively referred to as the biliary tract.

Most bile duct carcinomas are cancerous biliary epithelial cells covering the lumen; chemotherapy and radiotherapy have a little effect on the carcinomas and surgical resection with early detection is only curative treatment. However, there is no symptom for early bile duct carcinoma, for example, extrahepatic bile duct carcinoma is often found in a state of advanced cancer since symptoms, such as jaundice and itching, do not occur until the bile duct is obstructed by the progress of the carcinoma with bile flowed back into the blood vessel. On the other hand, intrahepatic bile duct carcinoma does not quite obstruct the extrahepatic bile duct, and thus, carcinoma often progresses while remaining asymptomatic without jaundice symptoms. According to statistics on cancer death rates by site in Japan in 2014 disclosed by the Center for Cancer Control and Information Services, National Cancer Center, the number of people dying of gallbladder/bile duct carcinoma amounted to 18,117, and the 5-year relative survival rate by site in 2003 to 2005 was 22.5% for males and 19.9% for females, being the second worst after pancreatic cancer. The bile duct is closely related to important organs, such as the liver and the pancreas, and thus, the metastasis of carcinoma to these organs contributes to the aggravation of prognosis.

Less-invasive abdominal ultrasonography and hematological examination are generally used for the diagnosis of biliary tract carcinoma (Non-patent Document 1). The rate of visualization of bile duct carcinoma by abdominal ultrasonography ranges from 21 to 90%, and it is considered problematic that the visualization rate reduces when the occupation site is the lower bile duct. Hematological examination using an increase in a tumor marker, such as CEA or CA19-9, as an index is carried out, but these tumor markers do not enable the early detection of biliary tract carcinoma and have a problem with diagnostic accuracy. Recently, a method has been reported for detecting bile duct carcinoma using the expression level of specific microRNA (miRNA) as an index (Patent Document 1).

Carcinoembryonic antigen (CEA) is known to be one of the embryonal antigens produced from carcinoma cells and be a glycoprotein having a molecular weight of around 200,000. CEA has 10 or more structurally similar subfamilies, and CEACAM1 is known as one of them. CEACAM1 in serum is reported to be usable as a marker for pancreatic carcinoma diagnosis (Non-patent Document 2), but the relation between CEACAM1 and extrahepatic bile duct carcinoma or the like has not previously been known.

PRIOR ART DOCUMENTS

Patent Document

Patent Document 1 Japanese unexamined Patent Application Publication No. 2015-139440

Non-Patent Documents

Non-patent Document 1 "Evidence-based clinical practice guidelines for the management of biliary tract cancers, Revised second edition", Edited by publishing committee of the clinical practice guidelines for the management of biliary tract cancers, Igaku Tosho Shuppan Co., Ltd., 2014, p. 38-39.

Non-patent Document 2 Simeone, D. M. et al., Pancreas. (2007) 34 (4): 436-443.

SUMMARY OF THE INVENTION

Object to be Solved by the Invention

An object of the present invention is to provide a method for collecting highly accurate data for diagnosis, useful in diagnosing the presence or absence of extrahepatic bile duct carcinoma or the like, and a kit for diagnosis.

Means to Solve the Object

To solve the above objects, the present inventors have analyzed the concentration of CEACAM1 in blood samples collected from extrahepatic bile duct carcinoma, intrahepatic bile duct carcinoma, and gallbladder carcinoma patients, and as a result, have found that the presence or absence of extrahepatic bile duct carcinoma, intrahepatic bile duct carcinoma, or gallbladder carcinoma can be determined with good accuracy using the CEACAM1 concentration as an index, thereby accomplishing the present invention.

Thus, the present invention is as follows.

1. A method for collecting data for diagnosing extrahepatic bile duct carcinoma, intrahepatic bile duct carcinoma, or gallbladder carcinoma, comprising a step of detecting the concentration of CEACAM1 in a blood sample collected from a test subject.

2. The method according to 1. above, further comprising a step of comparing the concentration of CEACAM1 in the blood sample collected from the test subject with the concentration of CEACAM1 in a blood sample derived from a non-carcinoma control subject, wherein the concentration of CEACAM1 in the blood sample collected from the test subject being higher than the concentration of CEACAM1 in the blood sample derived from the non-carcinoma control subject indicates that the test subject has a high possibility of having extrahepatic bile duct carcinoma, intrahepatic bile duct carcinoma, or gallbladder carcinoma.

3. The method according to 2. above, wherein the non-carcinoma control subject is a healthy subject, a biliary tract benign disease patient, or a serous cystadenoma patient.

4. The method according to 1. above, wherein:
when collecting data for diagnosing extrahepatic bile duct carcinoma, the concentration of CEACAM1 in the blood sample collected from the test subject being more than 63.9 ng/mL indicates that the test subject has a high possibility of having extrahepatic bile duct carcinoma;
when collecting data for diagnosing intrahepatic bile duct carcinoma, the concentration of CEACAM1 in the blood sample collected from the test subject being more than 55.0 ng/mL indicates that the test subject has a high possibility of having intrahepatic bile duct carcinoma;
and when collecting data for diagnosing gallbladder carcinoma, the concentration of CEACAM1 in the blood sample collected from the test subject being more than 49.9 ng/mL indicates that the test subject has a high possibility of having gallbladder carcinoma.

5. The method according to 4. above, wherein:
when collecting data for diagnosing extrahepatic bile duct carcinoma, the concentration of CEACAM1 in the blood sample collected from the test subject being more than 71.5 ng/mL indicates that the test subject has a high possibility of having extrahepatic bile duct carcinoma;
and when collecting data for diagnosing intrahepatic bile duct carcinoma or gallbladder carcinoma, the concentration of CEACAM1 in the blood sample collected from the test subject being more than 63.9 ng/mL indicates that the test subject has a high possibility of having intrahepatic bile duct carcinoma or gallbladder carcinoma.

6. The method according to 4. above, wherein the concentration of CEACAM1 in the blood sample collected from the test subject being more than 74.0 ng/mL indicates that the test subject has a high possibility of having extrahepatic bile duct carcinoma, intrahepatic bile duct carcinoma, or gallbladder carcinoma.

7. The method according to any one of 1. to 6. above, wherein the blood sample is serum.

8. The method according to any one of 1. to 7. above, wherein the extrahepatic bile duct carcinoma is extrahepatic bile duct carcinoma classified into stages I to IIB.

9. The method according to any one of 1. to 8. above, further comprising a step of detecting the concentration of CEA and/or CA19-9 in the blood sample collected from the test subject.

10. The method according to any one of 1. to 9. above, further comprising a step of detecting CEACAM1 in an extrahepatic bile duct, intrahepatic bile duct, or gallbladder tissue sample collected from the test subject.

11. A kit for diagnosing extrahepatic bile duct carcinoma, intrahepatic bile duct carcinoma, or gallbladder carcinoma, comprising an antibody specifically binding to CEACAM1 or a labeled product thereof.

12. The kit according to 11. above, further comprising an antibody specifically binding to CEA and/or CA19-9 or a labeled product thereof.

12. The kit according to 11. or 12. above, wherein the extrahepatic bile duct carcinoma is extrahepatic bile duct carcinoma classified into stages I to IIB.

Other embodiments of the present invention can include a method for diagnosing extrahepatic bile duct carcinoma, intrahepatic bile duct carcinoma, or gallbladder carcinoma, comprising detecting the concentration of CEACAM1 in a blood sample collected from a test subject.

Effect of the Invention

According to the present invention, highly accurate data for diagnosis, useful in diagnosing the presence or absence of extrahepatic bile duct carcinoma, intrahepatic bile duct carcinoma, or gallbladder carcinoma can be obtained, and thus extrahepatic bile duct carcinoma, intrahepatic bile duct carcinoma, or gallbladder carcinoma can be early detected and appropriately treated.

MODE OF CARRYING OUT THE INVENTION

Figure 1:
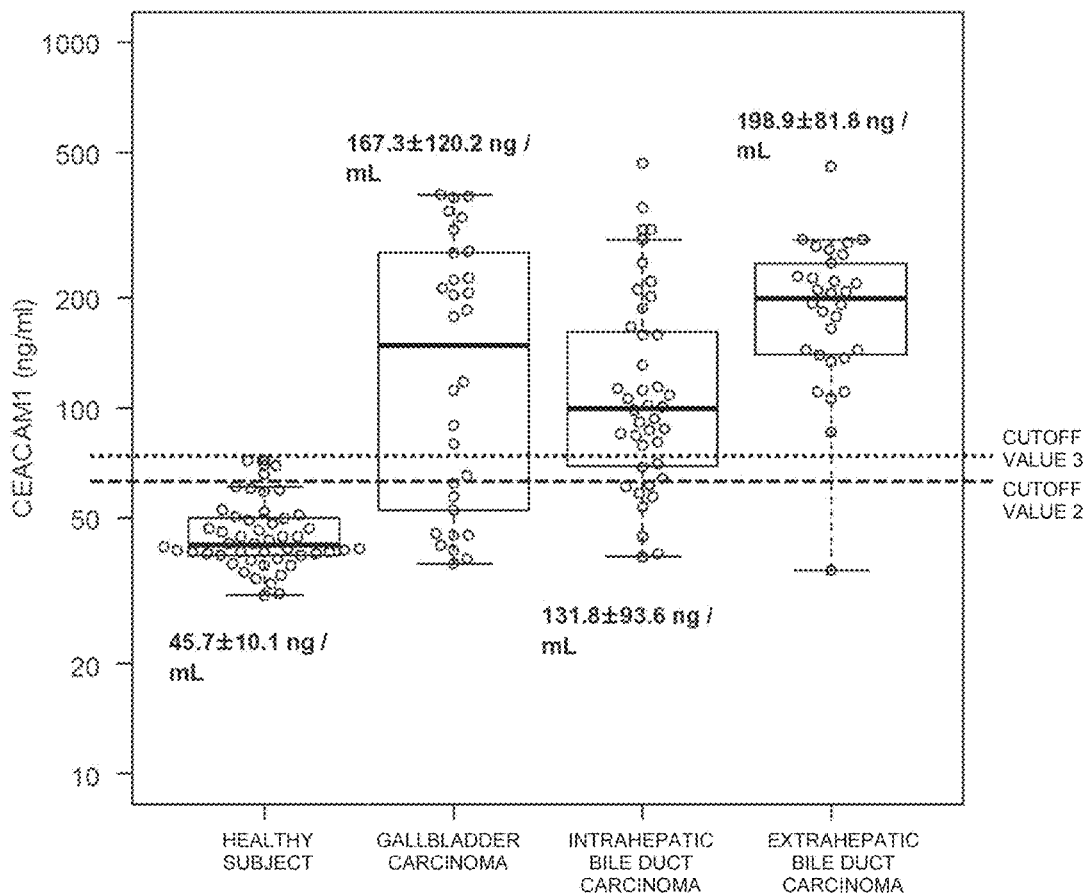
FIG. 1 is a graph showing the results of measuring the CEACAM1 concentration of the sera of 3 types of carcinoma patients (extrahepatic bile duct carcinoma, intrahepatic bile duct carcinoma, and gallbladder carcinoma) and healthy subject. In the figure, cutoff value 2 (65.9 ng/mL) and cutoff value 3 (76.0 ng/mL) indicate cutoff values for "CEACAM1 concentration average value+2SD" and "CEACAM1 concentration average value+3SD" in healthy subject, respectively

The method for collecting data for diagnosing extrahepatic bile duct carcinoma or the like according to the present invention is not particularly limited provided that it is a method for collecting data for diagnosing extrahepatic bile duct carcinoma or the like, comprising a step of detecting (and if necessary, further quantifying) the concentration of human CEACAM1 (carcinoembryonic antigen-related cell adhesion molecule 1) (also referred to as CD66a) in a blood sample collected from a test subject (donor) (hereinafter sometimes referred to as "collecting method of the present case"); examples of the blood sample can include blood and serum or plasma prepared from blood, and preferred is serum. The collecting method of the present case is a method for assisting the diagnosis of extrahepatic bile duct carcinoma or the like by a physician and does not include diagnostic action by a physician.

The kit for diagnosing extrahepatic bile duct carcinoma or the like according to the present invention is not particularly limited provided that it is a kit for use in diagnosing extrahepatic bile duct carcinoma or the like (hereinafter sometimes referred to as a "kit for diagnosis according to the present case"), comprising a an antibody specifically binding to human CEACAM1 in the blood sample (anti-human CEACAM1 antibody), or a labeled product thereof; the kit for diagnosis according to the present case is a use invention of a kit for diagnosing extrahepatic bile duct carcinoma or the like; and the kit typically includes package inserts, such as an instruction manual and a manual for diagnosing extrahepatic bile duct carcinoma or the like, in addition to components generally used in this type of kit for diagnosis, for example, a carrier, a pH buffering agent, and a stabilizer. The anti-human CEACAM1 antibody is preferably one specifically binding to CEACAM1 in an extrahepatic bile duct tissue sample, an intrahepatic bile duct tissue sample, or a gallbladder tissue sample collected from a test subject.

In the collecting method of the present case and the kit for diagnosis according to the present case, the carcinoma to be diagnosed may be at least one carcinoma selected from carcinomas in the biliary tract (bile duct and gallbladder), i.e., extrahepatic bile duct carcinoma, intrahepatic bile duct carcinoma, and gallbladder carcinoma, and the carcinoma also includes the 2 types of carcinomas of extrahepatic bile duct carcinoma and intrahepatic bile duct carcinoma, the 2 types of carcinomas of extrahepatic bile duct carcinoma and gallbladder carcinoma, the 2 types of carcinomas of intrahepatic bile duct carcinoma and gallbladder carcinoma, and the 3 types of carcinomas of extrahepatic bile duct carcinoma, intrahepatic bile duct carcinoma, and gallbladder carcinoma.

The extrahepatic bile duct carcinoma may be a state in which malignant cells (malignancy) occur in at least a part of a bile duct portion outside the liver (e.g., the perihilar bile duct or the distal bile duct); examples thereof can include perihilar bile duct carcinoma at stages I to IVB and distal bile duct carcinoma at stages IA to IV; preferred is extrahepatic bile duct carcinoma (perihilar bile duct carcinoma or distal bile duct carcinoma) classified into stages I to II (IIB) since the collecting method of the present case can also collect data for diagnosing relatively early extrahepatic bile duct carcinoma. The state of perihilar bile duct carcinoma and distal bile duct carcinoma at each stage is as shown in the following Tables 1 and 2, respectively.

TABLE 1

Perihilar Bile Duct Carcinoma

| Stage | State |
|---|---|
| I | A state in which carcinoma cells remain in the bile duct wall |
| II | A state in which carcinoma cells infiltrate beyond the bile duct wall but [1] do not infiltrate into other organs or [2] infiltrate only into the hepatic parenchyma |
| IIIA | A state in which carcinoma cells infiltrate into the portal vein in the bile duct infiltration dominant side or the hepatic artery |
| IIIB | A state in which carcinoma cells metastasize to regional lymph nodes |
| IVA | A state in which carcinoma cells infiltrate into bilateral secondary intrahepatic bile duct branches, the portal trunk, or the left and right branches |
| IVB | A state in which carcinoma cells metastasize distally |

TABLE 2

Distal Bile Duct Carcinoma

| Stage | State |
|---|---|
| IA | A state in which carcinoma cells remain in the bile duct wall |
| IB | A state in which carcinoma cells infiltrate beyond the bile duct wall but do not infiltrate into other organs |
| IIA | A state in which carcinoma cells infiltrate into the gallbladder, liver, pancreas, duodenum, or other surrounding organs, or blood vessels, such as the portal trunk, the superior mesenteric vein, and the inferior vena cava |
| IIB | A state in which carcinoma cells metastasize to regional lymph nodes |
| III | A state in which carcinoma cells infiltrate into the common hepatic artery, the coeliac artery, or the superior mesenteric artery |
| IV | A state in which carcinoma cells metastasize distally |

The intrahepatic bile duct carcinoma may be a state in which malignant cells (malignancy) occur in at least a part of a bile duct portion in the liver, and examples thereof can include intrahepatic bile duct carcinoma at stages I to IVB. The state of intrahepatic bile duct carcinoma at each stage is as shown in the following Table 3.

TABLE 3

Intrahepatic Bile Duct Carcinoma

| Stage | State |
|---|---|
| I | A state in which carcinoma cells are solitary and do not invade vascular vessels |
| II | A state in which carcinoma cells are solitary and do not invade vascular vessels [1], or a state in which carcinoma cells are multiple [2] |
| III | A state in which carcinoma cells infiltrate into the visceral peritoneum or surrounding organs |

TABLE 3-continued

Intrahepatic Bile Duct Carcinoma

| Stage | State |
|---|---|
| IVA | A state in which carcinoma cells infiltrate around the bile duct, or metastasize to lymph nodes |
| IVB | A state in which carcinoma cells metastasize distally |

The gallbladder carcinoma may be a state in which malignant cells (malignancy) occur in at least a part of the gallbladder, and examples thereof can include gallbladder carcinoma at stages 0 to IVB. The state of gallbladder carcinoma at each stage is as shown in the following Table 4.

TABLE 4

Gallbladder Carcinoma

| Stage | State |
|---|---|
| 0 | A state in which carcinoma cells remain in the gallbladder mucosa |
| I | A state in which carcinoma cells infiltrate into the lamina propria mucosae or the muscularis propria |
| II | A state in which carcinoma cells infiltrate into the subserosa or connective tissues around the gallbladder bed muscular layer |
| IIIA | A state in which carcinoma cells infiltrate into the serous membrane, the hepatic parenchyma, and/or one surrounding organ |
| IIIB | A state in which carcinoma cells metastasize to regional lymph nodes |
| IVA | A state in which carcinoma cells infiltrate into 2 or more surrounding organs other than the liver, or the portal trunk, the common hepatic artery, or the proper hepatic artery |
| IVB | A state in which carcinoma cells metastasize distally |

Examples of the test subject can include test subjects for whom it is uncertain whether or not they have carcinoma, and carcinoma patients for whom it is uncertain whether they have extrahepatic bile duct carcinoma or the like. Such test subjects and carcinoma patients include test subjects and carcinoma patients who have had extrahepatic bile duct carcinoma or the like in the past and have experienced a complete cure of the carcinomas but for whom it is uncertain whether they have extrahepatic bile duct carcinoma or the like at testing.

In the collecting method of the present case, the CEACAM1 concentration of a blood sample collected from the test subject being higher than the concentration of CEACAM1 in a blood sample derived from the non-carcinoma control subject indicates that the test subject has a high possibility of having extrahepatic bile duct carcinoma, intrahepatic bile duct carcinoma, or gallbladder carcinoma. Thus, the collecting method of the present case preferably further comprises a step of comparing the concentration of CEACAM1 in a blood sample collected from the test subject with the concentration of CEACAM1 in a blood sample derived from the non-carcinoma control subject. Comprising such a comparison step enables the collection of data for diagnosing the test subject as having a high possibility of having extrahepatic bile duct carcinoma or the like when the CEACAM1 concentration of a blood sample derived from the test subject is higher than the CEACAM1 concentration of the blood sample derived from the non-carcinoma control subject, and enables the collection of data for diagnosing the test subject as having a low possibility of having extrahepatic bile duct carcinoma or the like when the CEACAM1 concentration of a blood sample derived from the test subject is not higher than the CEACAM1 concentration of a blood sample derived from the non-carcinoma control subject. In performing the collecting method of the present case, as the CEACAM1 concentration of the blood sample derived from the non-carcinoma control subject, one measured each time may be used, or one measured in advance may be used. The blood sample derived from the non-carcinoma control subject is preferably one obtained by collecting the same type of sample as the sample derived from the test subject and then subjecting it to the same treatment as that for the blood sample derived from the test subject.

The "non-carcinoma control subject" herein may be a subject not having carcinoma (a control for the test subject); specific examples thereof can include a healthy subject, a biliary tract benign disease patient, and a serous cystadenoma (SCA) patient.

In the collecting method of the present case, the CEACAM1 concentration of a blood sample collected from the test subject being higher than a threshold value (a cutoff value) indicates that the test subject has a high possibility of having extrahepatic bile duct carcinoma, intrahepatic bile duct carcinoma, or gallbladder carcinoma. The threshold value (cutoff value) cannot simply be determined because of varying depending on the type of the carcinoma to be diagnosed, the type of the blood sample, the detection method, and the like; however, it is typically about 40.0 ng/mL, preferably about 43.0 ng/mL, more preferably about 47.0 ng/mL, still more preferably about 50.0 ng/mL, yet more preferably about 51.9 ng/mL, particularly preferably about 57.0 ng/mL, particularly more preferably about 60.0 ng/mL, particularly still more preferably about 63.0 ng/mL, particularly yet more preferably about 65.9 ng/mL, and particularly preferably about 70.0 ng/mL, particularly more preferably about 73.5 ng/mL, most preferably about 76.0 ng/mL.

The range of "about" in the "about ** ng/mL" typically means the range of ±5 ng/mL, preferably the range of ±4 ng/mL, more preferably the range of ±3 ng/mL, still more preferably the range of ±2 ng/mL, most preferably the range of ±1 ng/mL.

In the collecting method of the present case, the threshold value (cutoff value) for indicating that the test subject has a high possibility of having extrahepatic bile duct carcinoma when the carcinoma to be diagnosed is extrahepatic bile duct carcinoma is preferably about 65.9 (specifically 63.9) ng/mL, more preferably about 73.5 (specifically 71.5) ng/mL, still more preferably about 76.0 (specifically 74.0) ng/mL. The threshold value (cutoff value) for indicating that the test subject has a high possibility of having intrahepatic bile duct carcinoma when the carcinoma to be diagnosed is intrahepatic bile duct carcinoma is preferably about 57.0 (specifically 55.0) ng/mL, more preferably about 65.9 (specifically 63.9) ng/mL, still more preferably about 76.0 (specifically 74.0) ng/mL. The threshold value (cutoff value) for indicating that the test subject has a high possibility of having gallbladder carcinoma when the carcinoma to be diagnosed is gallbladder carcinoma is preferably about 51.9 (specifically 49.9) ng/mL, more preferably about 65.9 (specifically 63.9) ng/mL, still more preferably about 76 (specifically 74.0) ng/mL.

Specific examples of the CEACAM1 can include one or more proteins selected from the following group A protein.

Group A Protein (1) a protein consisting of the amino acid sequence shown in SEQ ID NO: 1 (CEACAM1 isoform 2 [NCBI Reference Sequence: NP_001020083]), or a protein consisting of an amino acid sequence in which 1 or several amino acids are deleted, substituted and/or added in the amino acid sequence shown in SEQ ID NO: 1 and having a high expression level in the test subjects compared to that in the healthy subject;

(2) a protein consisting of the amino acid sequence shown in SEQ ID NO: 2 (CEACAM1 isoform 4 [NCBI Reference Sequence: NP_001171742]), or a protein consisting of an amino acid sequence in which 1 or several amino acids are deleted, substituted and/or added in the amino acid sequence shown in SEQ ID NO: 2 and having a high expression level in the test subject compared to that in the healthy subject;

(3) a protein consisting of the amino acid sequence shown in SEQ ID NO: 3 (CEACAM1 isoform 3 [NCBI Reference Sequence: NP_001171744]), or a protein consisting of an amino acid sequence in which 1 or several amino acids are deleted, substituted and/or added in the amino acid sequence shown in SEQ ID NO: 3 and having a high expression level in the test subject compared to that in the healthy subject;

(4) a protein consisting of the amino acid sequence shown in SEQ ID NO: 4 (CEACAM1 isoform 5 [NCBI Reference Sequence: NP_001171745]), or a protein consisting of an amino acid sequence in which 1 or several amino acids are deleted, substituted and/or added in the amino acid sequence shown in SEQ ID NO: 4 and having a high expression level in the test subject compared to that in the healthy subject;

(5) a protein consisting of the amino acid sequence shown in SEQ ID NO: 5 (CEACAM1 isoform 6 [NCBI Reference Sequence: NP_001192273]), or a protein consisting of an amino acid sequence in which 1 or several amino acids are deleted, substituted and/or added in the amino acid sequence shown in SEQ ID NO: 5 and having a high expression level in the test subject compared to that in the healthy subject;

(6) a protein consisting of the amino acid sequence shown in SEQ ID NO: 6 (CEACAM1 isoform 1 [NCBI Reference Sequence: NP_001703]), or a protein consisting of an amino acid sequence in which 1 or several amino acids are deleted, substituted and/or added in the amino acid sequence shown in SEQ ID NO: 6 and having a high expression level in the test subject compared to that in the healthy subject.

The "amino acid sequence in which 1 or several amino acids are deleted, substituted and/or added" means an amino acid sequence in which typically 1 to 10, preferably 1 to 7, more preferably 1 to 6, still more preferably 1 to 5, yet more preferably 1 to 4, particularly preferably 1 to 3, particularly more preferably 1 to 2, most preferably 1 amino acid is deleted, substituted and/or added.

In the collecting method of the present case, the CEA and/or CA19-9 concentration of a blood sample derived from the test subject being higher than the CEA and/or CA19-9 concentration, respectively, of a blood sample derived from the healthy subject indicates that the test subject has a high possibility of having extrahepatic bile duct carcinoma or the like. In the collecting method of the present case, the detection of CEACAM1 in an extrahepatic bile duct tissue sample, an intrahepatic bile duct tissue sample, or a gallbladder tissue sample collected from the test subject indicates that the test subject has a high possibility of having extrahepatic bile duct carcinoma or the like. Thus, to further enhance the reliability of data for diagnosing extrahepatic bile duct carcinoma or the like, the collecting method of the present case preferably further comprises a step of simultaneously, successively, or separately detecting the concentration of CEA (carcinoembryonic antigen) (also referred to as CD66e or CEACAM5) and/or CA19-9 in a blood sample or a step of simultaneously, successively, or separately detecting and/or quantifying CEACAM1 in an extrahepatic bile duct tissue sample, an intrahepatic bile duct tissue sample and/or a gallbladder tissue sample.

Examples of the extrahepatic bile duct, intrahepatic bile duct, or gallbladder tissue sample can include fixed tissue sample sections, such as formalin-fixed paraffin sections and frozen sections.

In the collecting method of the present case, the method for detecting/quantifying the concentration of CEACAM1, CEA and/or CA19-9 in a blood sample or CEACAM1 in an extrahepatic bile duct tissue sample, an intrahepatic bile duct tissue sample, or a gallbladder tissue sample may be any method provided that it is a method capable of specifically detecting a part or all of CEACAM1 protein in a blood sample, or an extrahepatic bile duct tissue sample, an intrahepatic bile duct tissue sample, or a gallbladder tissue sample, or CEA and/or CA19-9 protein in a blood sample; specific examples thereof can include a mass spectrometric method for detecting peptides constituting CEACAM1, CEA and/or CA19-9 protein and an immunoassay method using an antibody specifically recognizing CEACAM1, CEA and/or CA19-9 protein.

Examples of the immunoassay method can suitably include an immunohistochemical staining method, an ELISA method, an EIA method, an RIA method, a western blotting method, and flow cytometry. Flow cytometry can be performed with a fluorescence activated cell sorter (FACS) using an antibody specifically binding to CEACAM1, CEA, or CA19-9 protein, labeled with a fluorescent substance (e.g., allophycocyanin [APC], phycoerythrin [PE], FITC [fluorescein isothiocyanate], Alexa Fluor 488, Alexa Fluor 647, Alexa Fluor 700, PE-Texas Red, PE-Cy5, or PE-Cy7).

To further enhance the reliability of data for diagnosing extrahepatic bile duct carcinoma or the like, the kit for diagnosis according to the present case preferably further comprises an antibody specifically binding to CEA and/or CA19-9 in a blood sample, or a labeled product thereof.

The antibody in the kit for diagnosis according to the present case may be an antibody, such as a monoclonal antibody, a polyclonal antibody, a human antibody, a chimeric antibody, or a humanized antibody, and also includes an antibody fragment consisting of a portion of an antibody, such as $F(ab')_2$, Fab, a diabody, Fv, ScFv, or $Sc(Fv)_2$.

Examples of the labeling substance in the labeled product in the kit for diagnosis according to the present case can include enzymes, such as peroxidase (e.g., horseradish peroxidase), alkaline phosphatase, β-D-galactosidase, glucose oxidase, glucose-6-phosphate dehydrogenase, alcohol dehydrogenase, malate dehydrogenase, penicillinase, catalase, apo-glucose oxidase, urease, luciferase, or acetylcholine esterase, fluorescent substances, such as fluorescein isothiocyanate, phycobiliprotein, rare earth metal chelate, dansyl chloride, and tetramethylrhodamine isothiocyanate, fluorescent proteins, such as green fluorescence protein (GFP), cyan fluorescence protein (CFP), blue fluorescence protein (BFP), yellow fluorescence protein (YFP), red fluorescence protein (RFP), and luciferase, radioactive isotopes, such as $^3H$, $^{14}C$, $^{125}I$, $^{131}I$, biotin, avidin, or chemiluminescent substances.

The present invention will be more specifically described below with reference to Examples. However, the technical scope of the present invention is not intended to be limited to these Examples.

EXAMPLES

Example 1

Using the CEACAM-1 concentration of a blood sample as an index, it was examined whether or not extrahepatic bile duct carcinoma, intrahepatic bile duct carcinoma, or gallbladder carcinoma could be determined.

Material

Serum samples of extrahepatic bile duct carcinoma patients were prepared according to an established method by collecting blood from total 30 extrahepatic bile duct carcinoma patients (24 males aged 40 to 84 and 6 females aged 70 to 81), 4 for stage I, 1 for stage IB, 8 for stage II, 3 for stage IIA, 4 for stage IIB, 1 for stage IIIA, 4 for stage IIIB, 3 for stage IVA, and 2 for stage IVB.

Serum samples of intrahepatic bile duct carcinoma patients were prepared according to the established method by collecting blood from total 40 intrahepatic bile duct carcinoma patients (23 males aged 47 to 80 and 17 females aged 55 to 85), 4 for stage I, 4 for stage II, 3 for stage III, 3 for stage IVA, 1 for stage IVB, and 25 for "not excised". The patients for "not excised" indicate carcinoma patients who were found to have more advanced carcinoma and many metastases by diagnostic imaging or the like and thus were considered to be incapable of being saved even by surgery and did not undergo surgery.

Serum samples of gallbladder carcinoma patients were prepared according to the established method by collecting blood from total 30 gallbladder carcinoma patients (13 males aged 57 to 86 and 17 females aged 46 to 80), 1 for stage I, 5 for stage II, 1 for stage IIIA, 1 for stage IIIB, 1 for stage IVA, 2 for stage IVB, and 19 for "not excised".

Serum samples of healthy subject as controls were prepared according to the established method by collecting blood from 50 healthy subject (9 males aged 37 to 66 and 41 females aged 23 to 60)

Serum samples of patients with biliary tract benign diseases (cholecystitis and autoimmune cholangitis) as controls were prepared according to the established method by collecting blood from 18 biliary tract benign disease patients (10 males aged 48 to 79 and 8 females aged 19 to 71).

Serum samples of serous cystadenoma (SCA) patients as controls were prepared according to the established method by collecting blood from 11 SCA patients (2 males aged 50 to 67 and 9 females aged 39 to 81).

Method

The CEACAM-1 concentration of the serum samples was measured using "Human CEACAM-1/CD66a DuoSet ELISA" (from R&D Systems, Inc.) according to the protocol appended to the product. The CEA concentration and the CA19-9 concentration of the serum samples as comparative controls, which were measured according to an established method, were obtained from SRL, Inc. Cutoff values for the CEACAM1 concentration for distinguishing between patients with 3 types of carcinomas (extrahepatic bile duct carcinoma, intrahepatic bile duct carcinoma, and gallbladder carcinoma) and healthy subject were calculated based on the ROC curve using a statistical analysis software (the pROC package of R software) in addition to the "average±2× standard deviation (SD)" (FIG. 1, and FIGS. 6-8) and "average±3× SD" (FIG. 1, and FIGS. 6-8 and Tables 5 to 7) of the CEACAM1 concentrations in the healthy subject (FIGS. 1, 2B, 3B, 4B, and 6-8). Hereinafter, the cutoff value calculated based on the ROC curve is referred to as "cutoff value 1", and the cutoff values calculated based on the "average±2× SD" and the "average±3× SD" are referred to as "cutoff values 2 and 3", respectively.

Result

Figure 2A:
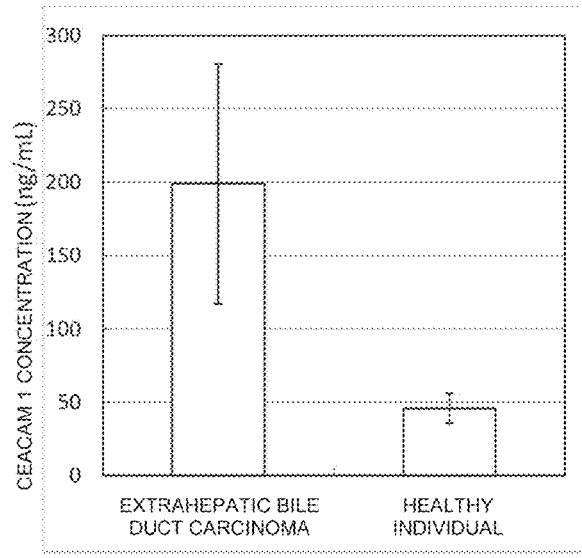
FIG. 2A is a graph showing the results of measuring the CEACAM1 concentration of the sera of extrahepatic bile duct carcinoma patients and healthy individuals (subject).
Figure 2B:
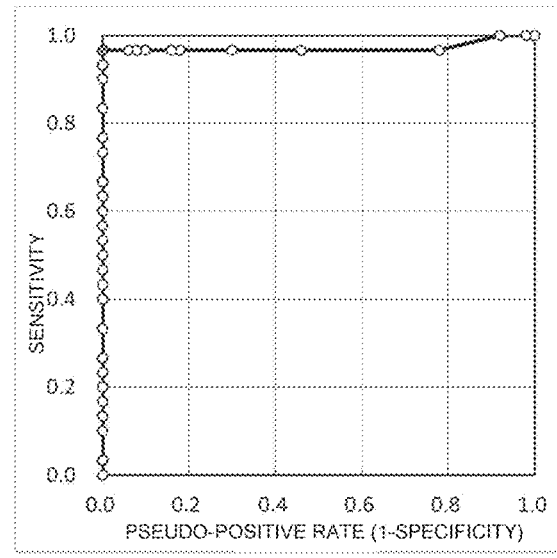
FIG. 2B is a graph showing the results of preparing receiver operating characteristic (ROC) curves based on the results of the CEACAM1 concentration of the sera of extrahepatic bile duct carcinoma patients and healthy subject.
Figure 3A:
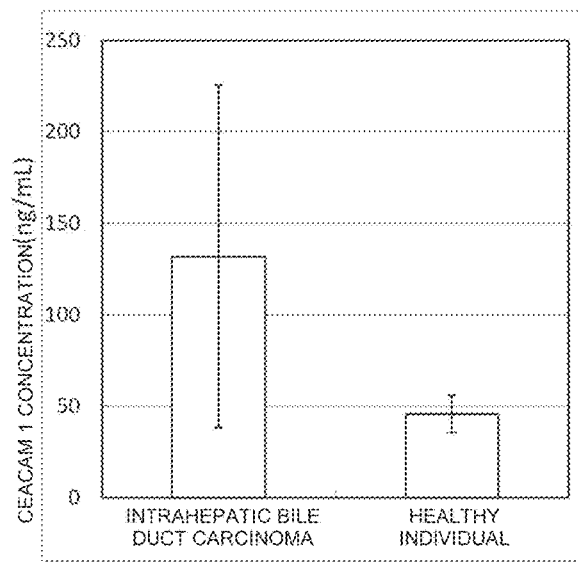
FIG. 3A is a graph showing the results of measuring the CEACAM1 concentration of the sera of intrahepatic bile duct carcinoma patients and healthy individuals (subject).
Figure 3B:
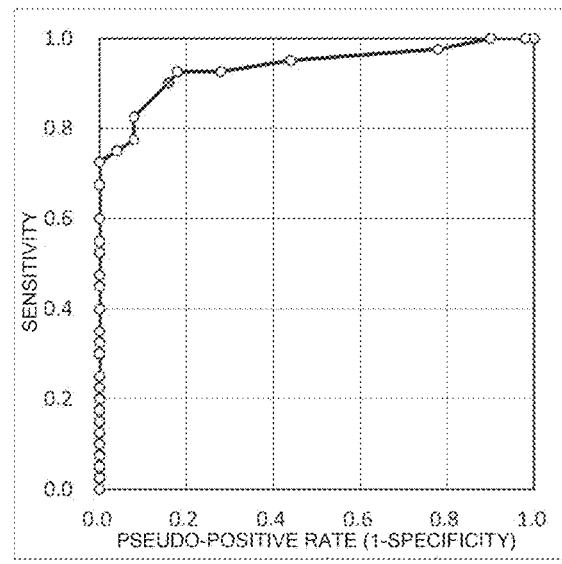
FIG. 3B is a graph showing the results of preparing ROC curves based on the results of the CEACAM1 concentration of the sera of intrahepatic bile duct carcinoma patients and healthy subject.
Figure 4A:
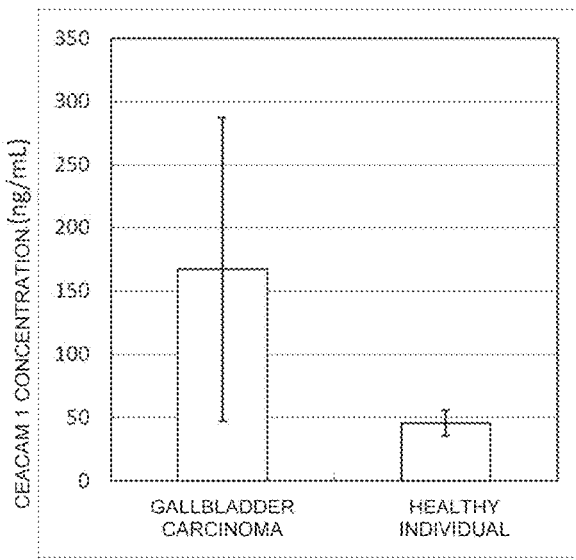
FIG. 4A is a graph showing the results of measuring the CEACAM1 concentration of the sera of gallbladder carcinoma patients and healthy individuals (subject).
Figure 4B:
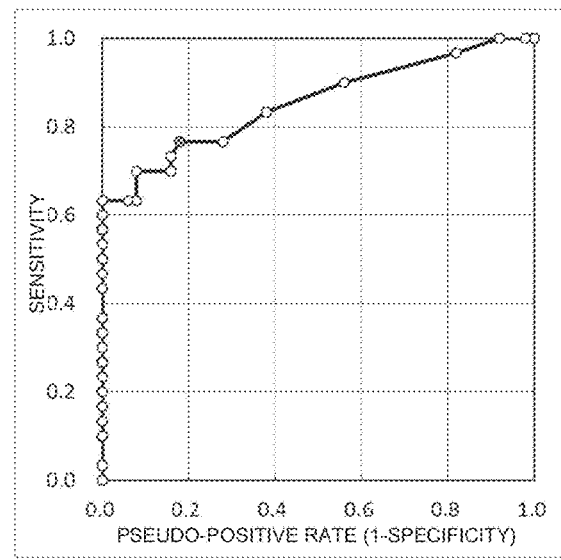
FIG. 4B is a graph showing the results of preparing ROC curves based on the results of the CEACAM1 concentration of the sera of gallbladder carcinoma patients and healthy subject.
Figure 5:
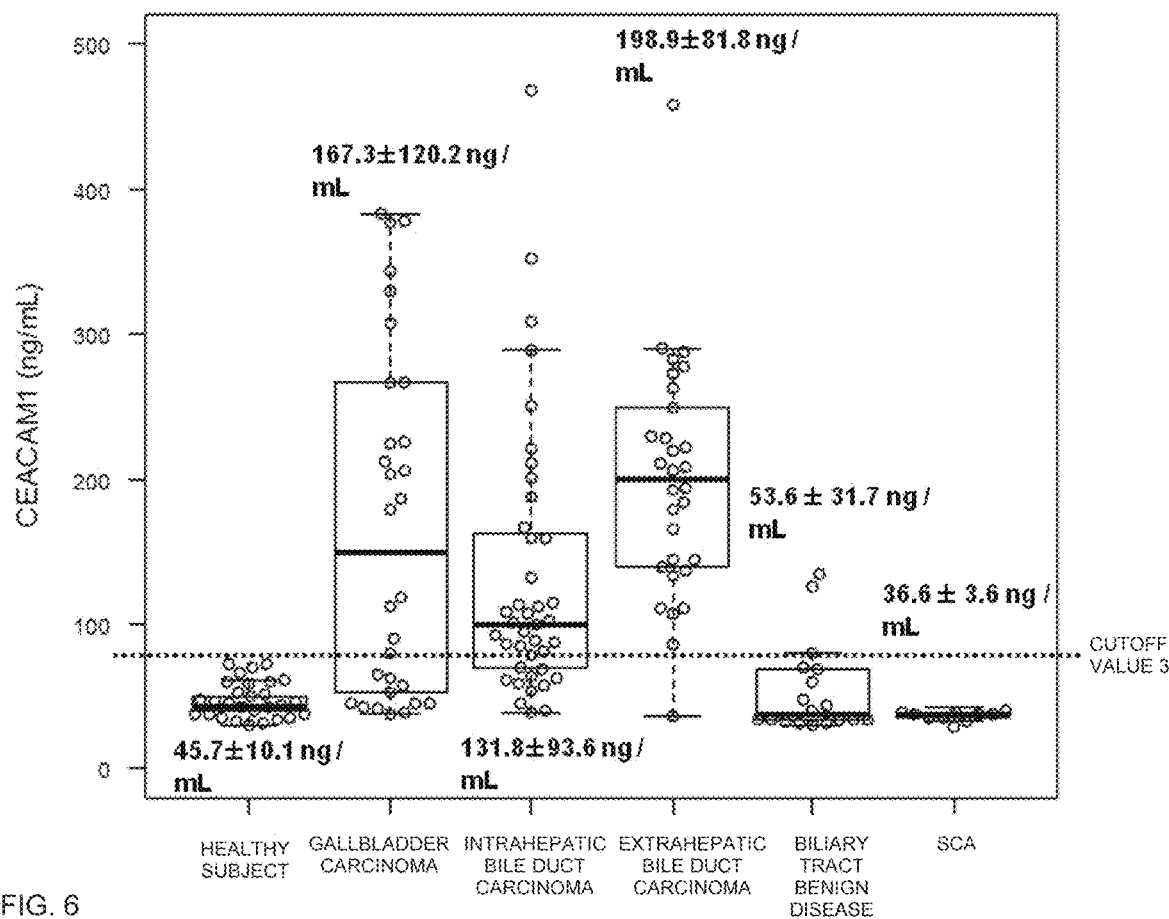
FIG. 5 is a graph showing the results of measuring the CEACAM1 concentration of the sera of biliary tract benign disease patients and serous cystadenoma (SCA) patients in addition to the results shown in FIG. 1. The cutoff value 3 in the figure represents 76.0 ng/mL.

1. Serum CEACAM-1 Concentration of Extrahepatic Bile Duct Carcinoma, Intrahepatic Bile Duct Carcinoma, and Gallbladder Carcinoma Patients The CEACAM-1 concentrations (average±SD) of the sera derived from the non-carcinoma control subject (healthy subject, biliary tract benign disease patients, and SCA patients) were 45.7±10.1 (30.8 to 72.4 ng/mL) (FIGS. 2A, 3A, and 4A), 53.6±31.7 (29.7 to 134.0 ng/mL), and 36.6±3.6 (29.1 to 42.3 ng/mL), respectively, whereas those in the sera derived from patients with 3 types of carcinomas (extrahepatic bile duct carcinoma, intrahepatic bile duct carcinoma, and gallbladder carcinoma) were 198.9±81.8 (36.1 to 458.1 ng/mL) (FIG. 2A), 131.8±93.6 (39.2 to 468.2 ng/mL) (FIG. 3A), and 167.3±120.2 (37.4 to 383.2 ng/mL) (FIG. 4A), respectively (FIGS. 1 and 5).

These results show that the CEACAM-1 concentration of blood samples of patients with 3 types of carcinomas (extrahepatic bile duct carcinoma, intrahepatic bile duct carcinoma, and gallbladder carcinoma) is high compared to that for subject not having carcinoma (healthy subject, biliary tract benign disease patients, and SCA patients).

Diagnosis of Extrahepatic Bile Duct Carcinoma, Intrahepatic Bile Duct Carcinoma, and Gallbladder Carcinoma.

Then, cutoff values for distinguishing between carcinoma patients and healthy subject were set to measure sensitivity and specificity. Specifically, when the cutoff value 1 for extrahepatic bile duct carcinoma was set to 73.5 ng/mL, the sensitivity (the percentage of test-positive patients in extrahepatic bile duct carcinoma patients) and specificity (the percentage of test-negative patients in patients not having extrahepatic bile duct carcinoma [healthy subject]) for extrahepatic bile duct carcinoma were 96.7% and 100%, respectively. Similarly, when the cutoff value 2 for extrahepatic bile duct carcinoma was 65.9 ng/mL, the sensitivity and the specificity were 96.7% and 92.0%, respectively; when the cutoff value 3 for extrahepatic bile duct carcinoma was 76.0 ng/mL, the sensitivity and the specificity were 96.7% and 100%, respectively.

When the cutoff value 1 for intrahepatic bile duct carcinoma was set to 57.0 ng/mL, the sensitivity and the specificity for intrahepatic bile duct carcinoma were 90.0% and 84.0%, respectively. Similarly, when the cutoff value 2 for intrahepatic bile duct carcinoma was 65.9 ng/mL, the sensitivity and the specificity were 77.5% and 92.0%, respectively; when the cutoff value 3 for intrahepatic bile duct carcinoma was 76.0 ng/mL, the sensitivity and the specificity were 72.5% and 100.0%, respectively.

When the cutoff value 1 for gallbladder carcinoma patients was set to 51.9 ng/mL, the sensitivity and the specificity for gallbladder carcinoma were 76.7% and 82.0%, respectively. Similarly, when the cutoff value 2 for gallbladder carcinoma was 65.9 ng/mL, the sensitivity and the specificity were 63.3% and 92.0%, respectively; when the cutoff value 3 for gallbladder carcinoma was 76.0 ng/mL, the sensitivity and the specificity were 63.3% and 100.0%, respectively.

These results show that when the concentration of CEACAM1 in blood samples is measured and suitable cutoff values are set, 3 types of carcinomas (extrahepatic bile duct carcinoma, intrahepatic bile duct carcinoma, and gallbladder carcinoma) can be diagnosed using the CEACAM1 concentration as an index. Particularly, for the diagnosis of extrahepatic bile duct carcinoma, when around 73.5 to 76.0 ng/mL is set as a cutoff value, the sensitivity and the specificity are as very high as 96.7% and 100%, respectively, showing that extrahepatic bile duct carcinoma can be diagnosed with good accuracy.

3. Relation with Stage of Carcinoma

Figure 6:
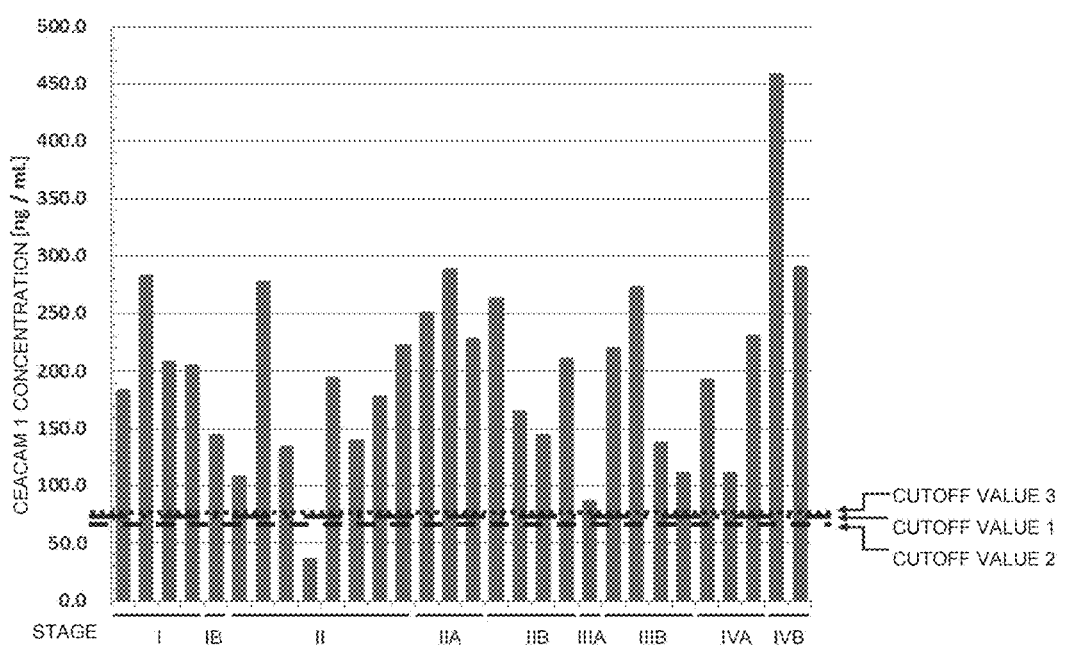
FIG. 6 is a graph showing the relationship between the CEACAM1 concentration of the sera of extrahepatic bile duct carcinoma patients (vertical axis) and the stage of the carcinoma (horizontal axis). The cutoff values 1 to 3 in the figure represent 73.5, 65.9, and 76.0 ng/mL, respectively.
Figure 7:
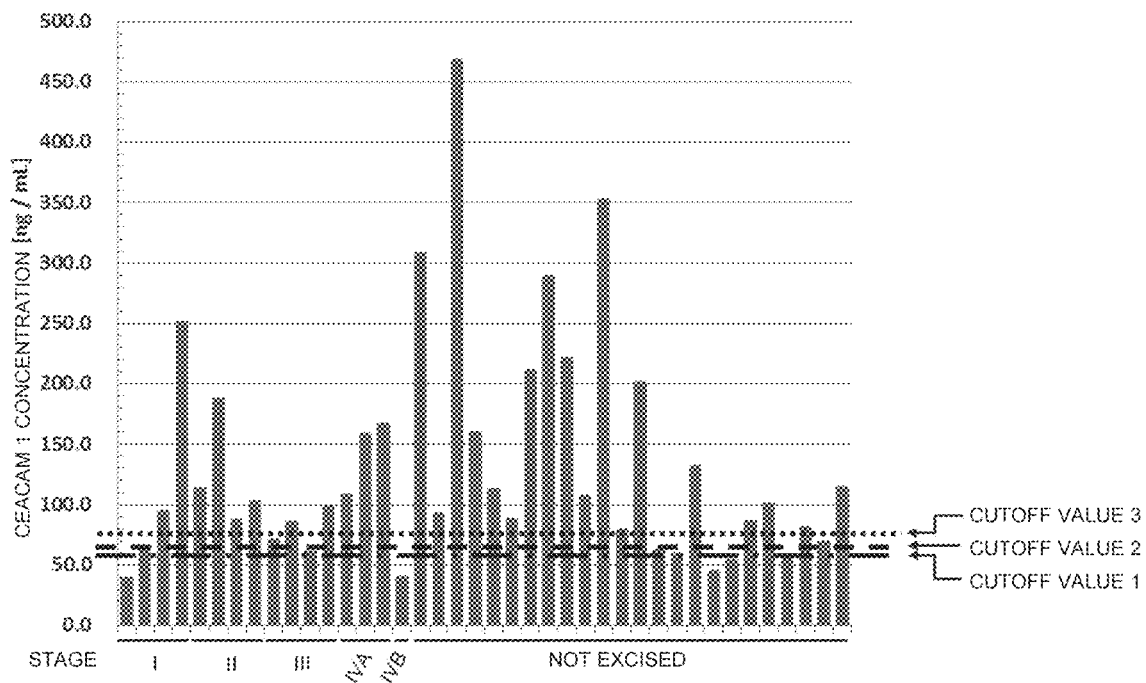
FIG. 7 is a graph showing the relationship between the CEACAM1 concentration of the sera of intrahepatic bile duct carcinoma patients (vertical axis) and the stage of the carcinoma (horizontal axis). The cutoff values 1 to 3 in the figure represent 57.0, 65.9, and 76.0 ng/mL, respectively.
Figure 8:
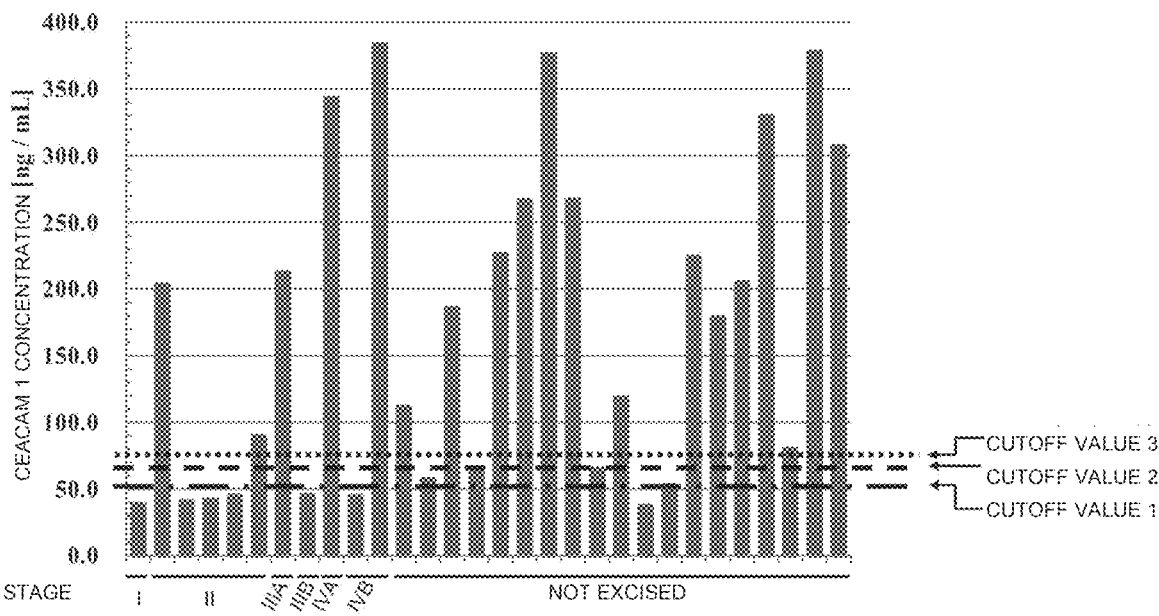
FIG. 8 is a graph showing the relationship between the CEACAM1 concentration of the sera of gallbladder carcinoma patients (vertical axis) and the stage of the carcinoma (horizontal axis). The cutoff values 1 to 3 in the figure represent 51.9, 65.9, and 76.0 ng/mL, respectively.

Then, the relation between the CEACAM1 concentration and the stage of carcinoma was examined. The positive rates (sensitivities) of 3 types of carcinomas (extrahepatic bile duct carcinoma, intrahepatic bile duct carcinoma, and gallbladder carcinoma) had high values irrespective of the degree of progression of carcinoma when any of the cutoff values 1 to 3 described above was set (FIGS. 6 to 8). Particularly, the positive rate of extrahepatic bile duct carcinoma had a high value (95% [=100×19/20]) even for relatively early extrahepatic bile duct carcinoma at stages I to IIB (FIG. 6).

These results show that relatively early extrahepatic bile duct carcinoma, intrahepatic bile duct carcinoma, and gallbladder carcinoma can be diagnosed using the concentration of CEACAM1 in blood samples as an index.

4. Comparison and Combination with Other Carcinoma Diagnosis Marker

Similar to CEACAM1, CEA and CA19-9 are known as tumor markers. Accordingly, the CEA concentration and the CA19-9 concentration of the sera of patients with 3 types of carcinomas (extrahepatic bile duct carcinoma, intrahepatic bile duct carcinoma, and gallbladder carcinoma) were also measured for comparison with CEACAM1 for diagnostic accuracy.

As a result, in extrahepatic bile duct carcinoma patients, the positive rate of CEACAM1 alone (96.7%) ("CEACAM1-positive" in Table 5) was higher than the positive rate of CEA (20.0%) ("CEA-positive" in Table 5) or the positive rate of CA19-9 (60.0%) ("CA19-9-positive" in Table 5). In addition, 23 of 24 extrahepatic bile duct carcinoma patients showing CEA negativity were CEACAM1-positive ("CEA-negative+CEACAM1-positive" in Table 5), and 9 of 10 extrahepatic bile duct carcinoma patients showing CA19-9 negativity were CEACAM1-positive ("CA19-9-negative+CEACAM1-positive" in Table 5).

These results show that CEACAM1 is a marker capable of diagnosing extrahepatic bile duct carcinoma with better accuracy than CEA or CA19-9.

TABLE 5

Extrahepatic Bile Duct Carcinoma

| Marker Protein | Positive Rate (%) |
| --- | --- |
| CEA-positive | 20.0 (6/30) |
| CA19-9-positive | 60.0 (15/25) |
| CEACAM1-positive | 96.7 (29/30) |
| CEA-negative + CEACAM1-positive | 95.8 (23/24) |
| CA19-9-negative + CEACAM1-positive | 90.0 (9/10) |
| (CEA-negative + CA19-9-negative) + CEACAM1-positive | 87.5 (7/8) |

The "positive rate" indicates the percentage of test-positive patients in extrahepatic bile duct carcinoma patients when the cutoff value for the concentration of each marker protein in healthy subject is set to average ±3 × SD.

In intrahepatic bile duct carcinoma patients, the positive rate of a combination of CEACAM1 and CEA (84.2%) ("CEACAM1-positive+CEA-positive" in Table 6) and the positive rate of a combination of CEACAM1+CA19-9 (86.2%) ("CEACAM1-positive+CA19-9-positive" in Table 6) were high compared to the positive rate of CEACAM1 alone (72.5%) ("CEACAM1-positive" in Table 6). In addition, 15 of 22 intrahepatic bile duct carcinoma patients showing CEA negativity were CEACAM1-positive ("CEA-negative+CEACAM1-positive" in Table 6), and 3 of 7 intrahepatic bile duct carcinoma patients showing CA19-9 negativity were CEACAM1-positive ("CA19-9-negative+CEACAM1-positive" in Table 6).

These results show that CEACAM1 combined with CEA or CA19-9 is a marker capable of diagnosing intrahepatic bile duct carcinoma with good accuracy compared to the case of using CEACAM1 alone.

TABLE 6

Intrahepatic Bile Duct Carcinoma

| Marker Protein | Positive Rate (%) |
| --- | --- |
| CEACAM1-positive | 72.5 (29/40) |
| CEACAM1-positive + CEA-positive | 84.2 (32/38) |
| CEACAM1-positive + CA19-9-positive | 86.2 (25/29) |
| CEA-negative + CEACAM1-positive | 68.2 (15/22) |
| CA19-9-negative + CEACAM1-positive | 42.9 (3/7) |
| (CEA-negative + CA19-9-negative) + CEACAM1-positive | 50.0 (3/6) |

The "positive rate" indicates the percentage of test-positive patients in intrahepatic bile duct carcinoma patients when the cutoff value for the concentration of each marker protein in healthy subject is set to average ±3 × SD.

In gallbladder carcinoma patients, the positive rate of a combination of CEACAM1 and CEA (73.3%) ("CEACAM1-positive+CEA-positive" in Table 7) and the positive rate of a combination of CEACAM1+CA19-9 (87.5%) ("CEACAM1-positive+CA19-9-positive" in Table 7) were high compared to the positive rate of CEACAM1 alone (63.3%) ("CEACAM1-positive" in Table 7). In addition, 7 of 16 gallbladder carcinoma patients showing CEA negativity were CEACAM1-positive ("CEA-negative+CEACAM1-positive" in Table 7), and 3 of 6 gallbladder carcinoma patients showing CA19-9 negativity were CEACAM1-positive ("CA19-9-negative+CEACAM1-positive" in Table 7).

These results show that CEACAM1 combined with CEA or CA19-9 is a marker capable of diagnosing gallbladder carcinoma with good accuracy compared to the case of using CEACAM1 alone.

TABLE 7

Gallbladder Carcinoma

| Marker Protein | Positive Rate (%) |
| --- | --- |
| CEACAM1-positive | 63.3 (19/30) |
| CEACAM1-positive + CEA-positive | 73.3 (22/30) |
| CEACAM1-positive + CA19-9-positive | 87.5 (21/24) |
| CEA-negative + CEACAM1-positive | 43.8 (7/16) |
| CA19-9-negative + CEACAM1-positive | 50.0 (3/6) |
| (CEA-negative + CA19-9-negative) + CEACAM1-positive | 40.0 (2/5) |

The "positive rate" indicates the percentage of test-positive patients in gallbladder carcinoma patients when the cutoff value for the concentration of each marker protein in healthy subject is set to average ±3 × SD.

Example 2

It was examined whether or not extrahepatic bile duct carcinoma, intrahepatic bile duct carcinoma, or gallbladder carcinoma could be determined using the presence or absence of CEACAM-1 in an extrahepatic bile duct, intrahepatic bile duct, or gallbladder tissue sample as an index.

Material

Extrahepatic bile duct tissue samples of extrahepatic bile duct carcinoma patients were prepared as 10% formalin-fixed paraffin-embedded blocks (samples) according to an established method from 2 patients in whom the CEACAM-1 concentrations of serum samples were 283 ng/mL and 277 ng/mL, respectively among the 30 extrahepatic bile duct carcinoma patients analyzed in Example 1.

Intrahepatic bile duct tissue samples of intrahepatic bile duct carcinoma patients were prepared as 10% formalin-fixed paraffin-embedded samples according to the established method from 2 patients in whom the CEACAM-1 concentrations of serum samples were 250 ng/mL and 158 ng/mL, respectively among the 40 intrahepatic bile duct carcinoma patients analyzed in Example 1.

A gallbladder tissue sample of a gallbladder carcinoma patient was prepared as a 10% formalin-fixed paraffin-embedded sample according to the established method from 1 patient in whom the CEACAM-1 concentration of a serum sample was 212 ng/mL among the 30 gallbladder carcinoma patients analyzed in Example 1.

Method

Sections 3 mm in thickness were prepared from the 3 types of 10% formalin-fixed paraffin-embedded samples (the extrahepatic bile duct tissue sample of each extrahepatic bile duct carcinoma patient, the intrahepatic bile duct tissue sample of each intrahepatic bile duct carcinoma patient, and the gallbladder tissue sample of the gallbladder carcinoma patient), and subjected to immuno-histochemical staining on an automatic staining machine BOND-III (from Leica Microsystems) using an anti-human CEACAM-1 antibody (from R&D Systems, Inc., clone #: 283324, code #: MAB22441, dilution ratio: 1:500) and the Polymer Refine Detection Kit (from Leica Biosystems, code #: DS9800). Antigen activation treatment was not performed according to the preliminary examination of staining conditions. Samples in which human CEACAM-1 was stained were subjected to nuclear staining with hematoxylin.

Result

Figure 9:
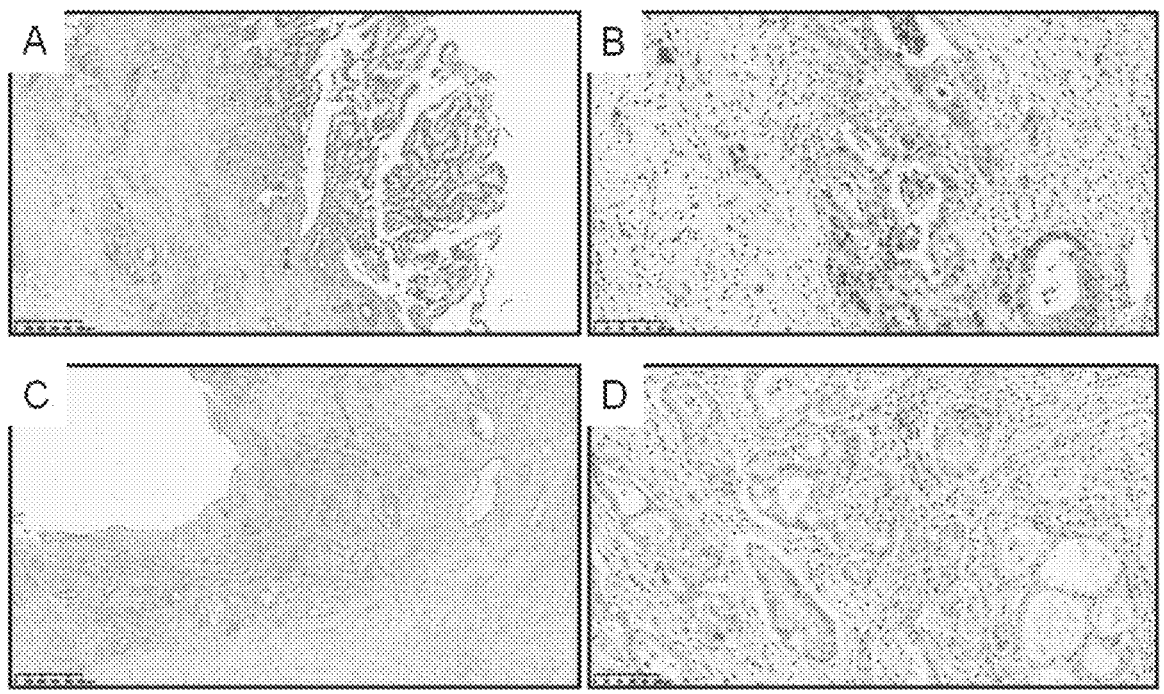
FIGS. 9(A) and 9(B) are microscopic images showing the results of immunohistochemically staining an extrahepatic bile duct tissue sample derived from an extrahepatic bile duct carcinoma patient for whom the CEACAM-1 concentration of the serum sample is 283 ng/mL.
FIGS. 9C and 9D are microscopic images showing the results of immunohistochemically staining an extrahepatic bile duct tissue sample derived from an extrahepatic bile duct carcinoma patient for whom the CEACAM-1 concentration of the serum sample is 277 ng/mL.
Figure 10:
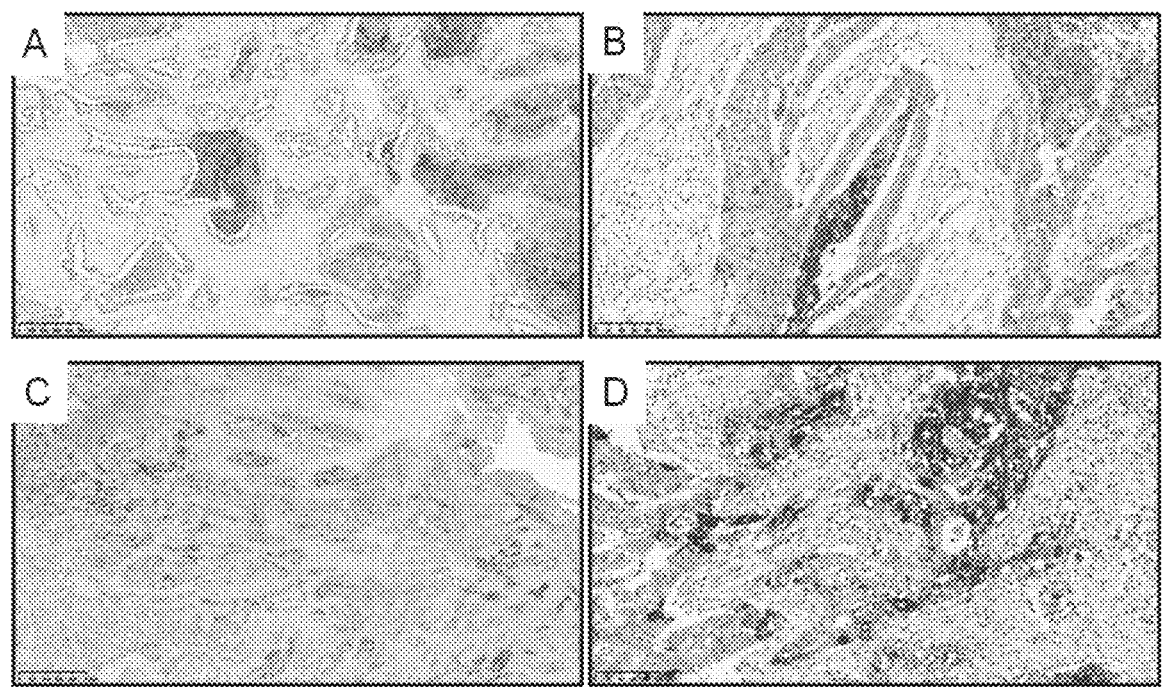
FIGS. 10(A) and 10(B) are microscopic images showing the results of immunohistochemically staining an intrahepatic bile duct tissue derived from an intrahepatic bile duct carcinoma patient for whom the CEACAM-1 concentration of the serum sample is 250 ng/mL.
FIGS. 10(C) and 10(D) are microscopic images showing the results of immunohistochemically staining an intrahepatic bile duct tissue derived from an intrahepatic bile duct carcinoma patient for whom the CEACAM-1 concentration of the serum sample is 158 ng/mL.
Figure 11:
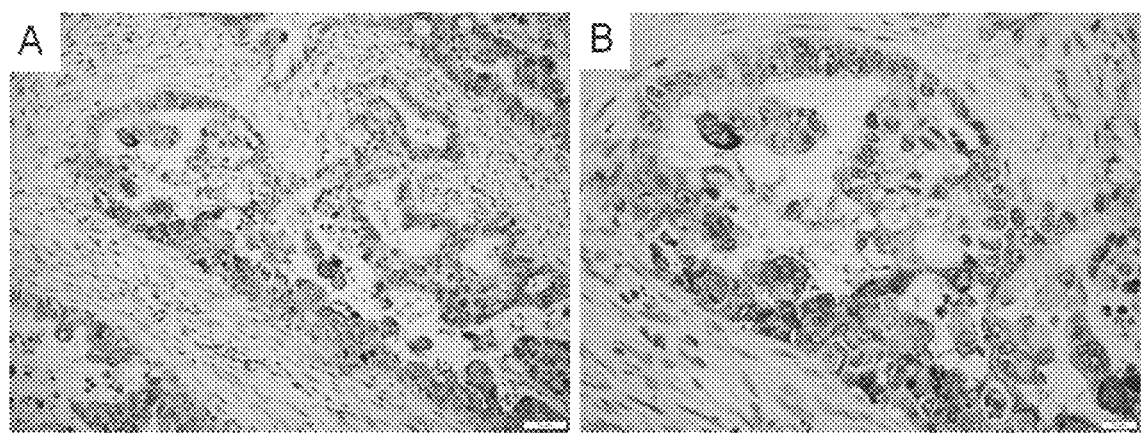
FIGS. 11(A) and 11(B) are microscopic images showing the results of immunohistochemically staining a gallbladder tissue derived from a gallbladder carcinoma patient for whom the CEACAM-1 concentration of the serum sample is 212 ng/mL.

All of the extrahepatic bile duct tissue sample of each extrahepatic bile duct carcinoma patient, the intrahepatic bile duct tissue sample of each intrahepatic bile duct carcinoma patient, and the gallbladder tissue sample of the gallbladder carcinoma patient were stained by the anti-human CEACAM-1 antibody (FIGS. 9 to 11). For example, in an example of intrahepatic bile duct carcinoma, CEACAM-1 was shown to be highly localized in the cytoplasm and cell membrane of carcinoma cells (FIG. 10(B)). In another example of intrahepatic bile duct carcinoma, CEACAM-1 was localized in the glandular cavity surface of carcinoma cells and appeared to be secreted into the glandular cavity (FIG. 10(D)). The background of immunostaining was little detected, showing that good and highly reliable staining data were obtained.

The above results show that extrahepatic bile duct carcinoma, intrahepatic bile duct carcinoma, or gallbladder carcinoma can be determined using the presence or absence of CEACAM-1 in an extrahepatic bile duct, intrahepatic bile duct, or gallbladder tissue sample as an index.

INDUSTRIAL APPLICABILITY

The present invention is conducive to the diagnosis and treatment of extrahepatic bile duct carcinoma, intrahepatic bile duct carcinoma, or gallbladder carcinoma.

The invention claimed is:

1. A method for diagnosing and treating gallbladder carcinoma in a subject, the method comprising:
   (a) measuring CEACAM1 levels in a blood sample of the subject;
   (b) detecting levels greater than 51.9±5 ng/mL in the blood sample and diagnosing the subject with a gallbladder carcinoma; and
   (c) surgically resecting the gallbladder carcinoma.

2. The diagnosis and treatment method according to claim 1, wherein the concentration of CEACAM1 in the blood sample is more than 65.9±5 ng/mL.

3. The diagnosis and treatment method according to claim 1, wherein the concentration of CEACAM1 in the blood sample is more than 76.0±5 ng/mL.

4. The diagnosis and treatment method according to claim 1, wherein the blood sample is serum.

5. The diagnosis and treatment method according to claim 1, wherein the gallbladder carcinoma patient is a gallbladder carcinoma patient whose blood sample is CEA and/or CA19-9 positive.

6. The diagnosis and treatment method according to claim 1, wherein the gallbladder carcinoma patient is a gallbladder carcinoma patient whose gallbladder carcinoma tissue sample is CEACAM1 positive.

\* \* \* \* \*